United States Patent
Monrabal

[11] Patent Number: 5,222,390
[45] Date of Patent: Jun. 29, 1993

[54] CRYSTALLIZATION ANALYSIS FRACTIONIZATION

[75] Inventor: Benjamin Monrabal, Terneuzen, Netherlands

[73] Assignee: The Dow Chemical Company, Midland, Mich.

[21] Appl. No.: 763,374

[22] Filed: Sep. 20, 1991

[51] Int. Cl.$^5$ ............... G01N 25/14; G01N 31/02
[52] U.S. Cl. ................................................. 73/61.76
[58] Field of Search ............... 73/61.76, 61.41, 53.01, 73/61.77

[56] References Cited

U.S. PATENT DOCUMENTS

4,226,114 10/1980 Hagedorn .................... 73/61.76
4,798,081 1/1989 Hazlitt et al. .................... 73/53.01
5,008,204 4/1991 Stehling ........................ 73/53.01 X

Primary Examiner—Hezron E. Williams
Assistant Examiner—Joseph W. Roskos
Attorney, Agent, or Firm—Ronald L. Hofer

[57] ABSTRACT

The composition distribution of a sample in solution is determined by basing the calculation of the composition distribution on intermittent measurements of the concentration of sample remaining in solution while precipitating the sample from the solution. An apparatus for determining the composition distribution of the sample has a sample solution vessel, a temperature control for raising and lowering the temperature of a solvent within the vessel, and a device for intermittently measuring concentration of sample in solution in the vessel.

11 Claims, 6 Drawing Sheets

FIG. 1.

Prior Art

CRYSTALLIZATION ANALYSIS FRACTIONIZATION

FIELD OF THE INVENTION

The present invention relates to an analytical method for analysis of crystallization, precipitation or extraction of soluble compounds as well as for studying crystallization kinetics. More particularly, the present invention relates to an analytical method for analyzing the composition distribution of polymers, for example, the short chain branching distribution in linear low density polyethylenes.

BACKGROUND OF THE INVENTION

A major application of the method and apparatus of the present invention is in the analysis of the composition of semi-crystalline polymers such as the analysis of short chain branching distribution (SCBD) in linear low density polyethylenes. This analysis is presently typically carried out by techniques such as Temperature Rising Elution Fractionization (TREF) or Analytical Temperature Rising Elution Fractionization (ATREF). See L. Wild and T.R. Ryle, *Polymer Preprints*, Am.-Chem.Soc.Polym.Chem.Div. 18,182 (1977). It is also known to combine ATREF with High Temperature Continuous Viscometry (HTCV) for analysis of polymers as is disclosed in U.S. Pat. No. 4,798,081 Jan. 17, 1989 to Hazlett et al.

Although TREF and ATREF techniques can be used for the analysis of polymers, these techniques are labor intensive and time consuming. In addition, the TREF and ATREF techniques require relatively complex apparatus. In the TREF and ATREF techniques a first sequential crystallization step is carried out to fractionate the sample in terms of branching content and then a second step is carried out in which the fractions are separated and analyzed to obtain the short chain branching distribution of the polymer. Typically, this analysis is carried out by crystallizing a solution as the temperature goes down which segregates the various fractions according to crystallinity. Once the crystallization has been completed, the short chain branching distribution information is contained in the segregated crystals, but an elution step must be carried out to retrieve and visualize the information. In the elution step, the temperature cycle is reversed and samples are eluted and analyzed for concentration as the temperature increases. The crystallization step often takes more than one day to carry out. The elution step adds further time to the method.

It will be appreciated that it is often highly desirable to complete an analysis as quickly as possible. It will also be appreciated that it is often desirable to process a large number of samples in a short time period. Of course, it is generally desirable to have a technique which is straightforward, which is not labor intensive, and which can be carried out using relatively inexpensive apparatus. For some uses it is desirable to have a technique which can be readily implemented in a quality control lab.

While the technique of the present invention is especially useful in composition distribution analysis in copolymers, broadly speaking, the technique provides a novel approach for analysis of the crystallization or precipitation of soluble compounds. Thus, the technique of this invention can be used to study crystallization kinetics, for solubility and extractable analysis of any solid chemical in a solvent, or for solvent elution analysis (molecular weight distribution) of polymers.

In accordance with the present invention, analysis is carried out at the same time that crystallization takes place by analyzing the remaining solution concentration as the solute precipitates out of solution. Hence, the analysis can be carried out relatively quickly. The present technique facilitates the processing of a relatively large number of samples using relatively inexpensive apparatuses and could be readily implemented in a quality control lab. Furthermore, this technique can be used for isothermal crystallization studies of polymer solutions or solutions of other chemical compounds. The technique provides a new approach to study solid/solvent interactions. Solubility and extractables can be easily measured automatically at various temperatures and, by using a solvent elution gradient, molecular weight distribution of polymers could also be measured.

Further understanding of the present invention will be had from the following description taken in conjunction with the accompanying claims and drawings. All percentages and parts herein are by weight unless specifically indicated otherwise.

SUMMARY OF THE INVENTION

In accordance with the present invention, an analytical method for analysis of precipitation of a soluble sample comprises the steps of:
(A) providing a sample in solution;
(B) precipitating the sample from the solution while intermittently measuring the concentration of sample remaining in the solution; and
(C) based on the results of step (B), calculating the composition distribution of the sample.

The apparatus of the present invention has:
(1) a sample solution vessel;
(2) temperature control means for raising and lowering the temperature of a solvent within said vessel; and
(3) solution concentration detection means for intermittently measuring concentration of sample remaining in solution within said vessel.

BRIEF DESCRIPTION OF THE DRAWING

FIG. 8 is a graphic representation of Example 2 showing a curve obtained from a LLDPE resin sample using the ATREF technique, which curve can be associated with the short chain branching distribution of the resin.

FIG. 9 is a graphic representation of Example 2 showing a curve corresponding to the cumulative short chain branching distribution curve obtained directly from concentration-temperature readings and the first derivative curve thereof corresponding to the crystallization distribution of the LLDPE resin which can be associated to the short chain branching distribution of the resin.

DESCRIPTION OF THE INVENTION

The composition distribution analysis in copolymers and study of crystallization kinetics is facilitated by the method and apparatus of the present invention which also provides an excellent tool for solubility and extractable analysis of solid chemicals in solvents and for solvent gradient elution analysis of polymers.

THE ANALYTICAL METHOD

Figure 1:
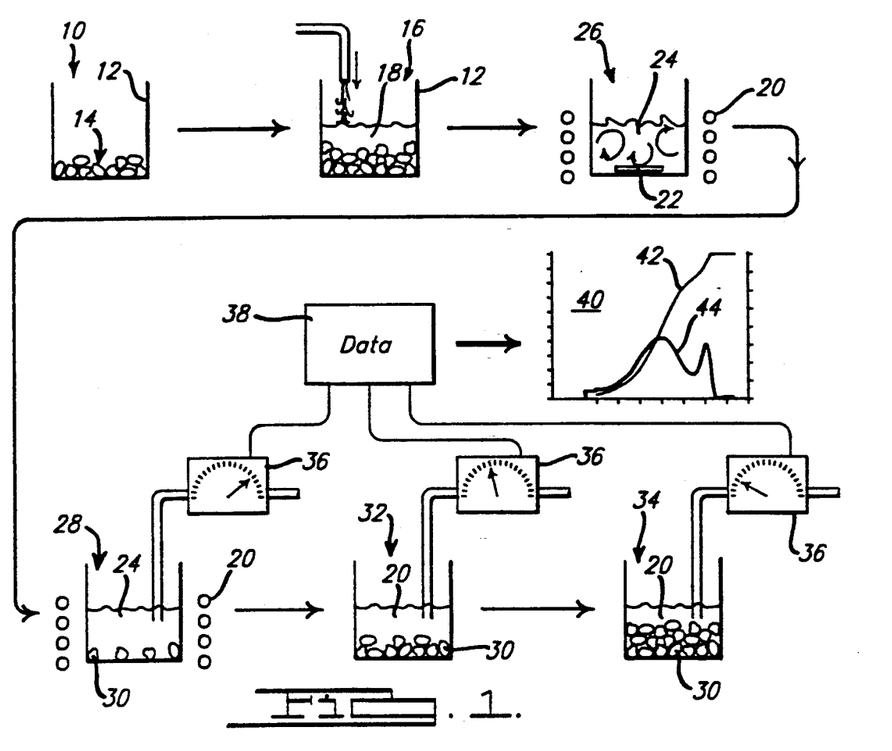
FIG. 1 is a somewhat diagrammatic flow chart schematically illustrating the method steps of a preferred embodiment of the present invention.

Now referring to FIG. 1, a preferred method of the present invention is represented in graphic illustration. First, as illustrated at 10, vessel 12 is provided with a sample 14 to be analyzed. Broadly speaking, materials suitable as samples for analysis in accordance with this invention include soluble compounds and preferably soluble polymers such as polypropylene or other polyolefins and their copolymers, for example, ethylene vinyl acetate, ethylene acrylic acid, as well as polyvinylidene chloride and methylcellulose and others. The method of this invention has been found to be especially useful to analyze semi-crystalline polymers such as linear low density polyethylene resin samples (LLDPE).

As illustrated at 16, a suitable solvent 18 is added to vessel 12. Suitable solvents will be readily apparent to those skilled in the art and include, but are not limited to, hydrocarbon and chlorinated hydrocarbon solvents. For example, a suitable solvent for a LLDPE is 1,2,4 trichlorobenzene. Sample 14 is then dissolved by adjusting the temperature of solvent 18 as necessary. For most samples, the solvent is heated by temperature control means 20 and agitated by stirring means 22 to dissolve sample 14 and thereby form solution 24 as indicated at 26. Then, as illustrated at 28, solution 24 is slowly cooled, continuously or step wise, by temperature control means 20 to precipitate a portion of sample 14 as precipitate 30 out of solution 24. Cooling and precipitation continue as indicated at 32 and 34 until a desired temperature value is reached. It should be noted that while dissolution is usually obtained by heating the solution, and precipitation or crystallization is usually obtained by cooling for some samples, such as methylcellulose, dissolution is obtained by cooling the solution and the sample is then precipitated by heating the solution.

Figure 3:
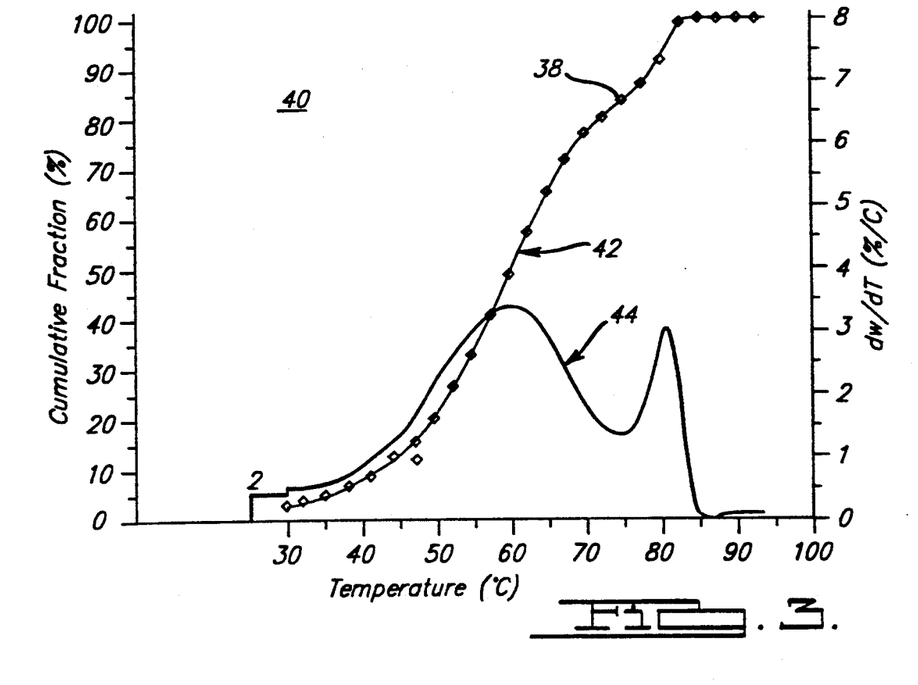
FIG. 3 is a graphic representation showing a curve corresponding to the cumulative short chain branching distribution curve directly obtained from the concentration-temperature reading, and the first derivative curve.

During the precipitation of sample 14 from solution 24, the concentration of sample 14 remaining in solution 24 is continuously or sequentially intermittently measured at 28, 32, 34, by detector 36 to obtain concentration data 38 which is plotted on graph 40 to define curve 42. Suspended sample should be filtered so that solution concentration can be obtained. The data is the cumulative composition distribution by subtraction. The last data point corresponds to the percent soluble fraction remaining at final temperature. The first derivative of curve 42 is curve 44 which represents the composition distribution analysis of sample 14. As will be understood by those skilled in the art, curve 44 corresponds to the short chain branching distribution of LLDPE with branches per 1000c's shown increasing leftward on the X-axis and the quantity of molecules of particular branching shown on the Y-axis. Graph 40 is shown in more detail in FIG. 3.

Figure 2:
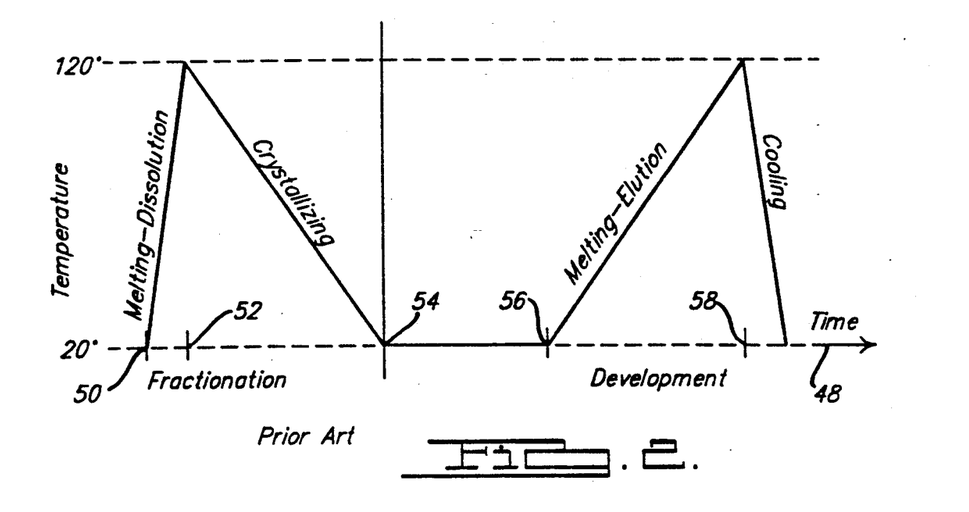
FIG. 2 is a graphic representation of a plot of temperature vs time comparing a preferred embodiment of the present invention and TREF of ATREF techniques.

The method of the present invention requires less time for carrying out an analysis than the TREF or ATREF methods, with only 1 temperature cycle needed. This time advantage of the present invention is illustrated in FIG. 2 along time line 48. Thus, a sample is first dissolved by heating beginning at time 50. At 120° C. and time 52, the dissolution is complete whereupon the temperature of the solution is reduced to crystallize and/or precipitate solute therefrom. In accordance with the method of the present invention, the concentration of solute in remaining solution is intermittently measured between time 52 and time 54 during the crystallization step and at time 54, it only remains to calculate the composition distribution. In the TREF and ATREF methods, however, the precipitate is further redissolved and eluted from time 56 to time 58 to develop the composition distribution.

APPARATUS

Figure 4:
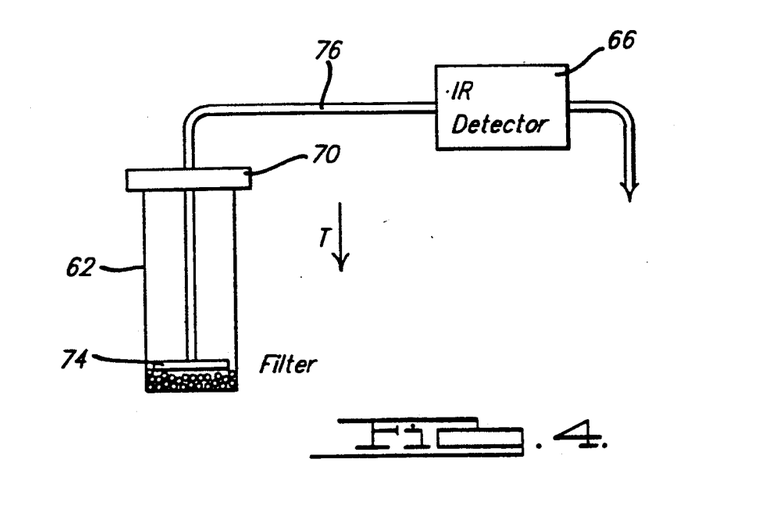
FIG. 4 is a schematic drawing of a preferred embodiment sample container and detector of the apparatus of the present invention.
Figure 5:
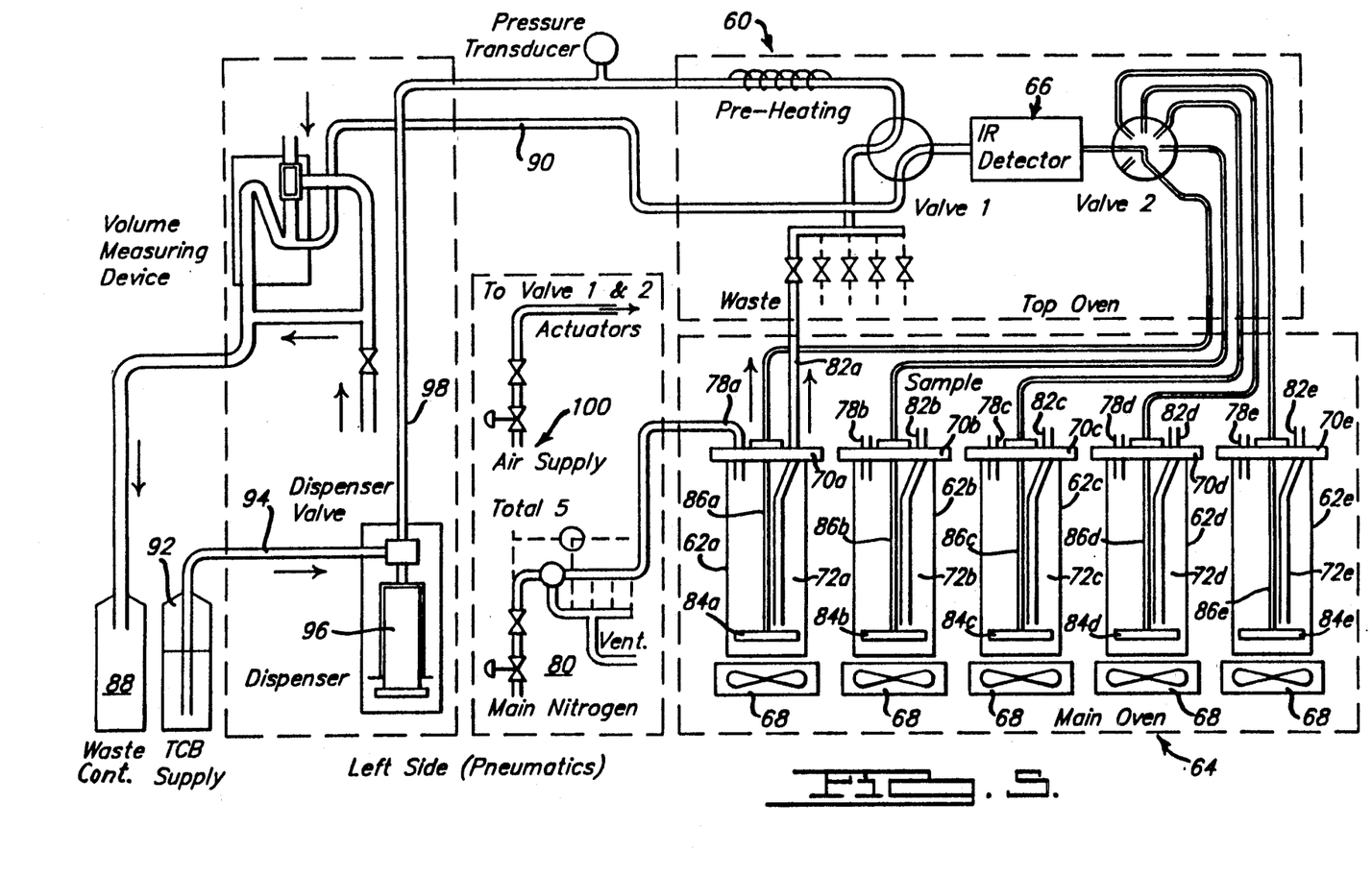
FIG. 5 is a schematic drawing of a preferred embodiment of an apparatus of the present invention.

An apparatus of the present invention is diagrammatically illustrated in FIGS. 4 and 5. Vessel 62 is sealed with cap 70 and the solution in vessel 62 is in fluid communication through filter 74 and conduit 76 with an infrared or other type of concentration detector 66 for determining solution concentration. An automated apparatus of this invention is shown in FIG. 5 and generally indicated by the numeral 60. FIG. 4 illustrates a vessel 62 with sample 14 therein. Apparatus 60 is fully automated and is an advantageous apparatus for carrying out the method of the present invention. Thus, apparatus 60 allows straightforward sample manipulation, and can handle the simultaneous analysis of multiple samples. Broadly speaking, apparatus 60 has a plurality of sample vessels 62, shown in FIG. 5 as 62a, 62b, 62c, 62d and 62e, temperature control means 64 for heating and cooling solvent in containers 62a-e to dissolve and precipitate samples from solution and solution concentration detecting means 66 for measuring the concentration of remaining solution during the precipitation of samples therefrom. Vessels 62a-e each have a magnetic stirrer 68 to provide agitation to solutions therein.

Vessels 62a-e have respective caps 70a-e for sealing their respective interiors, 72a-e. Each vessel 62a-e is in fluid communication through lines 78a-e with pressurized nitrogen source 80, through lines 82a-e with valve 1 and through filters 84a-e and lines 86a-e with valve 2.

Apparatus 60 also has waste container 88 in fluid communication with valve 1 through line 90 and solvent supply 92 which is in fluid communication through line 94, dispenser 96 and line 98 with valve 1. Valves 1 and 2 are air actuated by means illustrated diagrammatically at 100.

In operation of apparatus 60 for a composition distribution analysis of a copolymer, the samples of polymer are placed in each vessel 62a-e which are then sealed by respective caps 70a-e. Solvent is then drawn from supply 92 through line 94 and dispensed through line 98 to valve 1 and selectively dispensed to each vessel 62a-62e through lines 82a-82e or 86a-86e. The temperature of each vessel 62a will be raised to a preselected value by temperature control means 64 and stirrer 68 will be activated to thereby obtain dissolution of samples 14 in solution. After dissolution and temperature stabilization, temperature control means 64 will adjust the temperature of vessels 62a-62e downwardly at a preselected rate. Solution from each vessel 62a-62e is sampled intermittently through lines 86a-86e and valve 2 and the concentration thereof measured by IR detector 66. The concentration value is ascertained together with the temperature value at which the sample was taken. After measurement, the solution goes to waste container 88 through line 90. Concentration-temperature pair values are stored for plotting and calculation at the end of the experimental run. Crystals are separated from lines 86a-86e by filters 84a-84e. At the final temperature set-point, the calculation of the composition distribution analysis is done for all samples. Also, at the end of the experimental run, the apparatus 60 enters in an automatic cleaning mode. The temperature within the main oven goes up to 120° by temperature control means 64 to redissolve precipitate in remaining solution of containers 62a-62e which is then discarded by means of pressurized nitrogen with lines 78a-78e through lines 82a-82e and valve 1, actuated to a second position, to waste container 88. New solvent is dispensed from solvent supply 92 through lines 94 and 98 through valve 1, detector 66 and then valve 2, which is actuated to pass solvent through each of lines 86a-86e and filters 84a-84e to containers 62a-62e to finalize the cleaning of lines and container. This is followed up by a new discard to waste step which leaves the containers 62a-62e ready for the next experimental run. Further understanding of the present invention will be had from the following example.

EXAMPLE 1

The short chain branching distribution in a linear low density polyethylene (LLDPE) sample is analyzed as follows.

A sample of DOWLEX® brand LLDPE (DOWLEX® is a trademark of The Dow Chemical Company) with an average molecular weight of Mw 105000 and 0.920 density is weighed 207 milligrams±2 milligrams and introduced in one of the vessels (number 1) which is then closed (sealed). Other linear low density samples can be, if desired, analyzed at the same time by proper weighing and introduction in the remaining vessels.

The analysis is initiated by preheating the detector, valves and connecting lines to a temperature of 120° C. This is followed by the introduction of 75 mililiters of 1,2,4 trichlorobenzene in each selected vessel where a sample is to be analyzed. The pure solvent passing through the detector cell is used at this time to zero the detector signal. A filter type (3.5 microns) infrared spectrophotometer is used in this experiment where absorbance at 3.5 microns, corresponding to the C-H stretching vibration, provides the means to measure concentration of the polyethylene fractions dissolved in 1,2,4trichlorobenzene.

The main oven goes now to 120° C. where it will stay for one hour with stirrers at high speed (600 min-1) for sample dissolution. This is followed by cooling down to 95° C. at a 5 degrees C/min rate and a stabilization period of 40 minutes at this temperature before crystallization begins.

Crystallization is carried out from 95 down to 30° at 0.4 degrees C/minute cooling rate and held at 30° C. isothermal for another fifteen minutes, with a reduced stirring speed (300 min-1) maintained during the whole crystallization process.

During crystallization, sampling is carried out by applying nitrogen pressure (2 bars) to the individual vessels in connection with the proper positioning of the rotary valve (2). This results in the filtration and transfer of an aliquot of the solution to the detector and to a volume measuring device which by means of a capacitive sensor detects a preset volume of solution (0.7 mililiters in this experiment) and shuts down the nitrogen pressure to stop sampling. The detector reading (concentration) is recorded together with the sampling temperature and the volume measuring device is emptied to waste by means of air pressure through a solenoid valve. The rotary valve (2) can be then connected to the following container to repeat this process with a different polymer sample. The volume sampled is big enough to clean the common lines and detector cell (dead volume less than 0.4 mililiters) from the previous sample solution.

The five vessels can be analyzed at about every five minutes in a sequential manner to have at least twenty points for each polymer sample. In this particular experiment 27 data points (concentration-temperature) are taken between 95° and 45° C. at about every 1.9 degrees and 9 data points between 45 and the end of the experiment at about every 2.5 degrees (a total of 36 points for each vessel).

Figure 6:
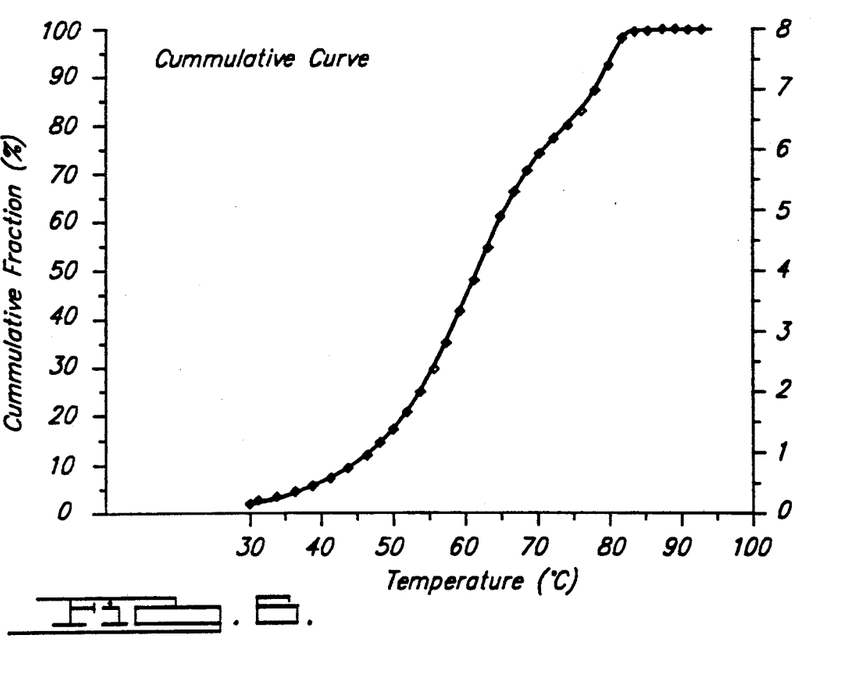
FIG. 6 is a graphic representation showing a curve corresponding to the cumulative short chain branching distribution curve directly obtained from the concentration-temperature readings of Example 1.

Table 1 shows the results for the DOWLEX® sample analyzed in vessel 1. The first six pair of values show a constant concentration (in absorbance units) as temperature goes down indicating that no significant crystallization takes place in this particular sample at temperatures above 86° C. Below this temperature the concentration is depressed, first with a steep slope, as shown in a smoothed graphic representation of table 1 data shown in FIG. 6 corresponding to the precipitation of the highly crystalline molecules with few or no branches in the main chain. This is followed by the precipitation of fractions of increasing branching content (lower crystallinity) as temperature is further reduced.

The concentration reading at the end of the experiment, 30° C., corresponds to the polymer fraction which remains soluble which is composed of highly branched or low molecular weight material.

Figure 7:
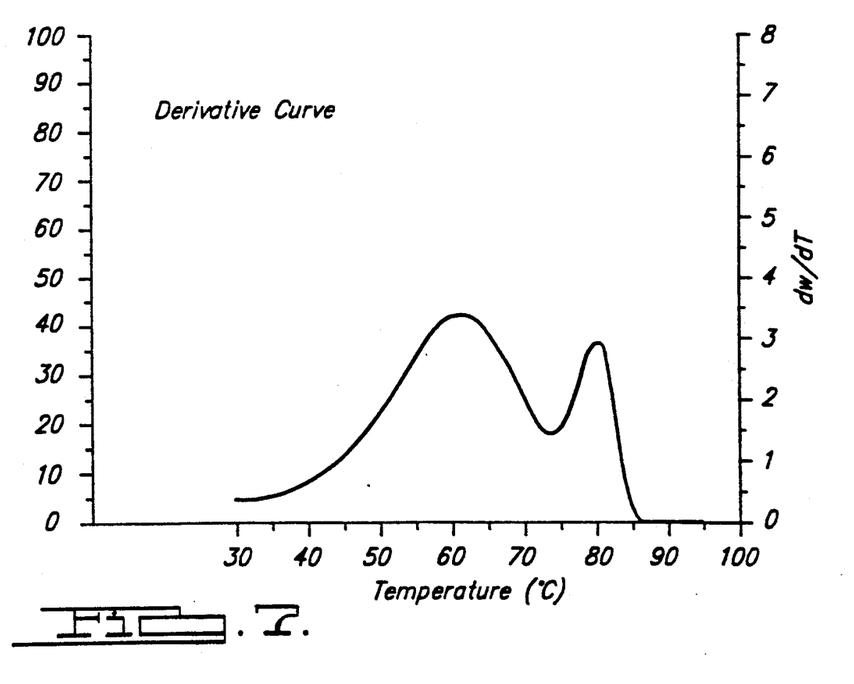
FIG. 7 is a graphic representation showing the first derivative curve of the curve of FIG. 6.

The first derivative of the concentration-temperature curve results in FIG. 7 corresponding to the crystallization distribution of that polymer sample which can be associated, as with the currently used techniques (TREF,ATREF), to the short chain branching distribution of the LLDPE resin.

TABLE 1

| Temperature (deg C.) | Concentration (abs. units) |
|---|---|
| 94.9 | 0.69577 |
| 93.1 | 0.64923 |

TABLE 1-continued

| Temperature (deg C.) | Concentration (abs. units) |
|---|---|
| 91.2 | 0.69352 |
| 89.3 | 0.69445 |
| 87.5 | 0.69449 |
| 85.6 | 0.69314 |
| 83.7 | 0.69110 |
| 81.9 | 0.68042 |
| 80.0 | 0.64153 |
| 78.1 | 0.60474 |
| 76.2 | 0.57602 |
| 74.4 | 0.55547 |
| 72.5 | 0.53628 |
| 70.6 | 0.51551 |
| 68.8 | 0.49067 |
| 66.9 | 0.46087 |
| 65.0 | 0.42528 |
| 63.2 | 0.38159 |
| 61.3 | 0.33545 |
| 59.4 | 0.29143 |
| 57.5 | 0.24730 |
| 55.7 | 0.20885 |
| 53.8 | 0.17491 |
| 51.9 | 0.14575 |
| 50.0 | 0.12116 |
| 48.2 | 0.10236 |
| 46.3 | 0.08372 |
| 43.8 | 0.06551 |
| 41.3 | 0.05089 |
| 38.8 | 0.03971 |
| 36.3 | 0.03079 |
| 33.8 | 0.02370 |
| 31.2 | 0.01840 |
| 29.9 | 0.01277 |
| 30.0 | 0.00965 |
| 30.0 | 0.01023 |

EXAMPLE 2

An LLDPE sample "A" is analyzed using conventional ATREF technique and the method and apparatus of the present invention using the procedures of Example 1. The results of the ATREF technique are graphically illustrated in FIG. 8. The results of the method and apparatus of the present invention are graphically illustrated in FIG. 9 and can be seen to be analogous, thus confirming the validity of the technique of the present invention.

EXAMPLE 3

Figure 10:
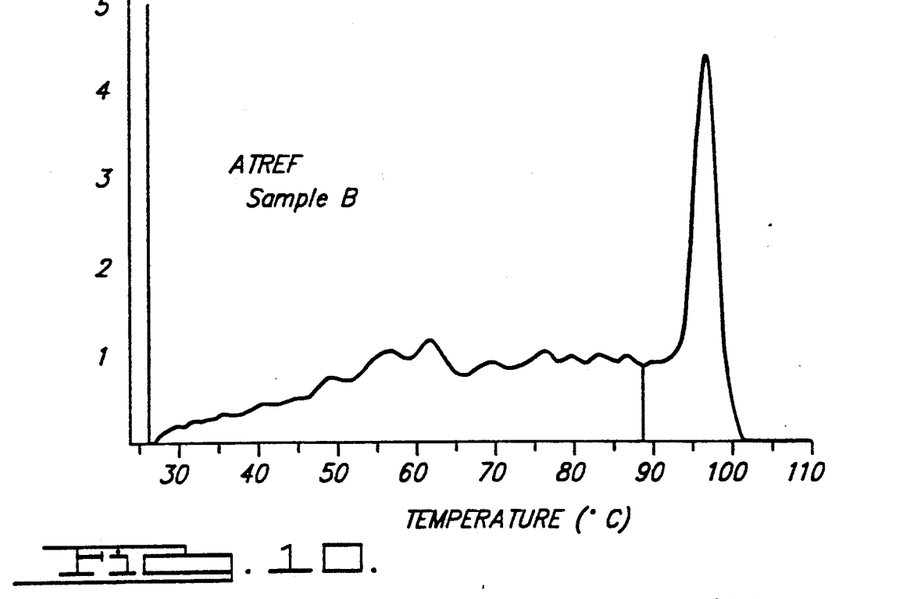
FIG. 10 is a graphic representation of Example 3 showing a curve obtained from a LLDPE resin sample using the ATREF technique, which curve can be associated with the short chain branching distribution of the resin.
Figure 11:
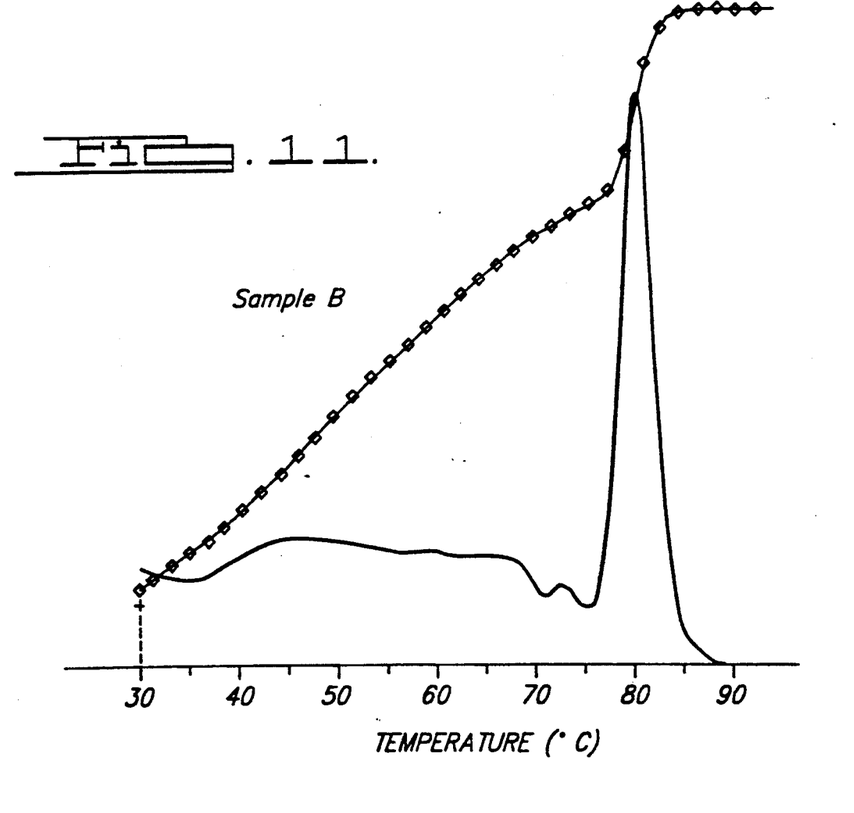
FIG. 11 is a graphic representation of Example 3 showing a curve corresponding to the cumulative short chain branching distribution curve obtained directly from concentration-temperature readings and the first derivative curve thereof corresponding to the crystallization distribution of the LLDPE resin which can be associated to the short chain branching distribution of the resin.

An LLDPE sample "B" is analyzed using conventional ATREF technique and the method and apparatus of the present invention using the procedures of Example 1. The results of the ATREF technique are graphically illustrated in FIG. 10. The results of the method and apparatus of the present invention are graphically illustrated in FIG. 11 and can be seen to be analogous, thus confirming the validity of the technique of the present invention.

What is claimed is:

1. An analytical method for analysis of precipitation of a soluble sample comprising the steps of:
   (A) providing a sample in solution;
   (B) precipitating the sample from the solution while intermittently measuring the concentration of sample remaining in the solution; and
   (C) based on the results of step (B), calculating the composition distribution of the sample.

2. The method of claim 1 wherein said sample is a soluble polymer.

3. The method of claim 2 wherein said sample is a semi-crystalline polymer.

4. The method of claim 3 wherein step (A) is carried out by heating a sample in a solvent.

5. The method of claim 4 wherein step (B) is carried out by decreasing the temperature of the solution.

6. The method of claim 5 wherein step (C) is carried out by measuring temperature-concentration data points to define a first curve and a second curve is calculated by taking the first derivative of said first curve to thereby obtain the composition distribution of said polymer.

7. The method of claim 6 wherein said sample is linear low density polyethylene and step (C) is carried out to calculate the short chain branching distribution thereof.

8. The method of claim 7 wherein said solvent is 1,2,4 trichlorobenzene or 0-dichlorobenzene.

9. The method of claim 8 wherein step (B) is carried out by cooling said solution at a rate of from about 0.02° to about 2° C. per minute.

10. An analytical method for analysis of precipitation of a plurality of soluble samples comprising the steps of:
    (A) providing said plurality of samples in separate solutions;
    (B) precipitating said samples from said solutions while intermittently and sequentially measuring the concentration of sample remaining in each solution; and
    (C) based on the results of step (B), calculating the composition of each sample.

11. An apparatus for analyzing the composition distribution of a soluble sample, said apparatus having:
    a sample vessel;
    temperature control means for raising and lowering the temperature of a solvent within said vessel; and
    solution concentration detection means for intermittently measuring concentration of sample remaining in a solution within said vessel.

* * * * *